(12) United States Patent
Watson et al.

(10) Patent No.: US 9,437,401 B2
(45) Date of Patent: Sep. 6, 2016

(54) SYSTEM AND METHOD FOR PLASMA TREATMENT USING DIRECTIONAL DIELECTRIC BARRIER DISCHARGE ENERGY SYSTEM

(71) Applicant: Plasmology4, Inc., Scottsdale, AZ (US)

(72) Inventors: Greg A. Watson, Sanford, FL (US); Jeffrey I. Meyers, Phoenix, AZ (US)

(73) Assignee: PLASMOLOGY4, INC., Scottsdale, AZ (US)

( * ) Notice: Subject to any disclaimer, the term of this patent is extended or adjusted under 35 U.S.C. 154(b) by 22 days.

(21) Appl. No.: 14/575,791

(22) Filed: Dec. 18, 2014

(65) Prior Publication Data

US 2016/0181069 A1     Jun. 23, 2016

Related U.S. Application Data

(60) Provisional application No. 61/919,218, filed on Dec. 20, 2013.

(51) Int. Cl.
*H01J 37/32* (2006.01)
*A61N 1/44* (2006.01)

(52) U.S. Cl.
CPC ........... *H01J 37/32348* (2013.01); *A61N 1/44* (2013.01)

(58) Field of Classification Search
CPC ............... H01J 37/32937; H01J 37/32125; H01J 37/32687
USPC ............. 315/111.01, 111.21, 111.41, 111.51, 315/111.71, 111.81
See application file for complete search history.

(56) References Cited

U.S. PATENT DOCUMENTS

| | | | |
|---|---|---|---|
| 6,099,523 A | 8/2000 | Kim et al. | |
| 6,361,748 B1 | 3/2002 | Prinz et al. | |
| 7,633,231 B2 | 12/2009 | Watson | |
| 7,679,027 B2 | 3/2010 | Bogatu | |
| 7,872,406 B2 * | 1/2011 | Matacotta | H01J 1/025 313/141 |
| 2008/0142057 A1 | 6/2008 | Yan et al. | |
| 2013/0068226 A1 | 3/2013 | Watson et al. | |

FOREIGN PATENT DOCUMENTS

DE     19532105 A1     3/1996
WO     2008082297 A1     7/2008

OTHER PUBLICATIONS

PCT ISR & WO for PCT/US2014/071703, mailed Mar. 17, 2015.

* cited by examiner

*Primary Examiner* — Tuyet Vo
(74) *Attorney, Agent, or Firm* — Fletcher Yoder, P.C.

(57) ABSTRACT

A system including a directional dielectric barrier discharge (DBD) energy system, including a first electrode assembly configured to generate energy, including a first housing having a first fluid disposed in a first chamber, a first magnet, wherein the first magnet is configured to help guide or contain the energy generated by the first electrode assembly, and a first dielectric barrier.

20 Claims, 5 Drawing Sheets

SYSTEM AND METHOD FOR PLASMA TREATMENT USING DIRECTIONAL DIELECTRIC BARRIER DISCHARGE ENERGY SYSTEM

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Modern medical systems enable physicians to treat a wide variety of diseases and ailments that are inside and outside of the body. Physicians may treat these diseases and ailments using topical treatments (e.g., treatments used on an exterior of a patient's body) or an internal treatment (e.g., surgery). Unfortunately, surgeries may be invasive, expensive, and require significant amounts of recovery time.

BRIEF DESCRIPTION OF THE DRAWINGS

Various features, aspects, and advantages of the present invention will become better understood when the following detailed description is read with reference to the accompanying figures in which like characters represent like parts throughout the figures, wherein.

DETAILED DESCRIPTION OF SPECIFIC EMBODIMENTS

Figure 1:
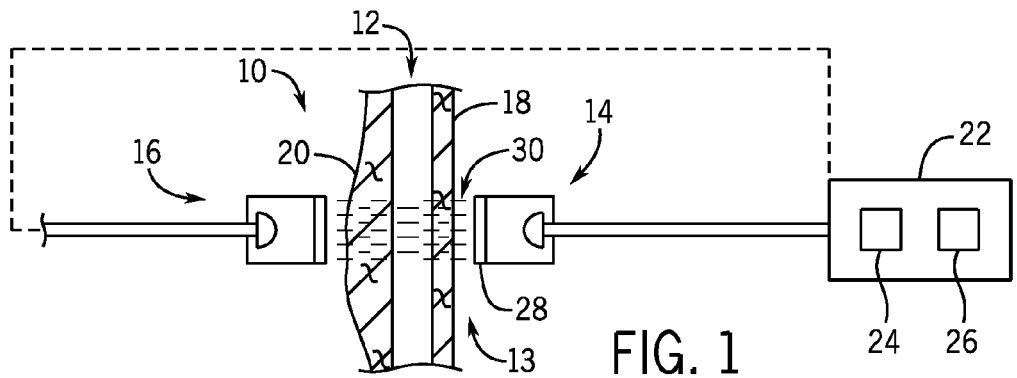
FIG. 1 is a cross-sectional side view of an embodiment of a directional dielectric barrier discharge energy system.

One or more specific embodiments of the present invention will be described below. These described embodiments are only exemplary of the present invention. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The disclosed embodiments include a directional dielectric barrier discharge (DBD) energy system capable of forming a non-thermal, multi-frequency, harmonic-rich plasma (e.g., a cold plasma with a temperature between approximately 60-80, 70-90, 80-100, 90-110, 100-120 degrees Fahrenheit) and/or multi-frequency, harmonic-rich RF energy. In operation, the directional DBD energy system controls and directs plasma by influencing the ions and electrons in the plasma stream as well as guiding radio frequency (RF) energy over a significant distance. For example, the directional DBD energy system may enable energy to penetrate deep into biological tissue (e.g., 1, 2, 3, 4, 5, 10, 20, 30, 40, or more centimeters) as well as expose a biological tissue surface to cold plasma. The directional DBD energy system may include at least one pair of powered and grounded electrode assemblies. In operation, the powered and grounded electrode assemblies are placed on opposite sides of a target substrate (e.g., biological tissue), enabling the grounded electrode assembly to attract the cold plasma and RF energy formed by the powered electrode assembly. In some embodiments, one or both of the electrodes may be spaced away from the substrate to form an air gap between the substrate and the electrodes. The air gap enables one or both of the electrodes to form a non-thermal, multi-frequency, harmonic-rich plasma out of the surrounding atmospheric gases, while simultaneously emitting multi-frequency, harmonic-rich RF energy. In operation, the non-thermal, multi-frequency, harmonic-rich plasma treats a substrate surface while electrons in the plasma and the multi-frequency, harmonic-rich RF energy penetrates deep into the substrate. In another embodiment, the electrodes may be placed in direct contact with the substrate to block plasma formation while enabling a multi-frequency, harmonic-rich RF energy to penetrate into and/or through the substrate. In some embodiments, the powered and grounded electrode assemblies may include magnets that contain and guide electrons in the cold plasma as well as RF energy through the biological tissue. For example, the directional DBD energy system may generate multiple coupled magnetic fields via embedded ferrous and/or electromagnets. It is believed that the magnetic fields formed by the magnets guides and focuses electrons as well as RF energy, enabling deep penetration of biological tissue (e.g., osteological, connective, muscle, nervous, and epithelial tissues) with the electrons and RF energy, which may enable faster healing from injury, trauma, and/or infection (e.g., internal bacterial infections, deep tissue injuries, bone fractures) without surgery or other invasive treatment. For example, the directional DBD system may non-invasively treat sub-dermal and osteological tissue infections by killing pathogens (e.g., bacteria), with energy that penetrates deeply into the target substrate and/or expose a biological tissue surface to cold plasma.

FIG. 1 is a cross-sectional side view of an embodiment of a directional dielectric barrier discharge (DBD) energy system 10. As explained above, the directional DBD energy system 10 may produce cold plasma and/or RF energy capable of penetrating deep into or through a target substrate 12 (e.g., osteological, connective, muscular, nervous, and epithelial tissues in humans and animals) to treat a plasma treatment area 13. For example, the dielectric DBD energy system 10 may treat chest, limbs, etc. of a patient. In some embodiments, the cold plasma and/or RF energy produced by the directional dielectric barrier discharge (DBD) energy system 10 may also change surface properties and/or characteristics of an interior of an object (e.g., human cavity, food product, medical material/device, etc.). The directional DBD energy system 10 may include a first electrode assembly 14 and a second electrode assembly 16. To facilitate energy transfer, the first and second electrode assemblies 14, 16 may be positioned on opposing sides (e.g., opposite first and second surfaces 18, 20) of the target substrate 12. In operation, a controller 22 coupled to the first electrode assembly 14 provides an electrical signal to the first electrode assembly 14 that enables the directional DBD energy system 10 to produce the cold plasma and energy. Specifically, the controller 22 uses a processor 24 to execute instructions stored in a memory 26 to produce and control the electrical signal (e.g., change power, amplitude, frequency/frequencies, pulse timing, etc.). In some embodiments, the electrical signal may be a multi-frequency, harmonic-rich signal (e.g., a timed pulse electrical signal pulsed between 100-700 Hz with an output voltage between 1-100 KV peak-peak having multiple A/C waves at multiple frequencies, that overlap to produce 2-2,000,000 or more harmonic components between DC and 500 MHz). As the first electrode assembly 14 receives the electrical signal, the first electrode assembly 14 may attenuate some of the frequencies as charge builds on a first dielectric barrier 28 of the assembly 14. Once the charge reaches a saturation point, the electrical signal crosses the first dielectric barrier 28 and an air gap 30 between the first electrode assembly 14 and the first side 18 (e.g., proximal side) of the target substrate 12 (e.g., electrical ground, ground potential). As the multi-frequency, harmonic-rich electrical signal crosses the air gap 30; the gas molecules/atoms lose and gain electrons to produce a cold plasma with positive ions, negative ions, and electrons. It is believed that the multi-frequency, harmonic-rich electrical signal facilitates removal of electrons from the molecules/atoms with less energy and heating than typical plasma formation. Accordingly, the plasma is a low temperature plasma or cold plasma (e.g., a cold plasma with a temperature between approximately 60-120, 60-80, 70-90, 80-100, 90-110, 100-120 degrees Fahrenheit), enabling exposure to a temperature sensitive target substrate 12 (e.g., biological tissue, polymer).

On the opposite side 20 (e.g., distal side) of the target substrate 12 is the grounded second electrode assembly 16 that attracts the plasma and energy from the first electrode assembly 14. The second electrode assembly 16 may be a powered or unpowered ground. For example, the second electrode assembly 16 may also couple to the controller 22. In operation, the controller 22 may adjust the voltage on the second electrode assembly 16 to increase the attraction of the cold plasma and energy to the second electrode assembly 16. In other words, the second electrode assembly 16 may assist in guiding and or drawing electrons in the plasma stream and energy from the first electrode assembly 14 through the target substrate 12. For example, the second electrode assembly 16 may enable energy and electron penetration through 1, 2, 3, 4, 5, 10, 20, 30, 40, or more centimeters of biological tissue.

Figure 2:
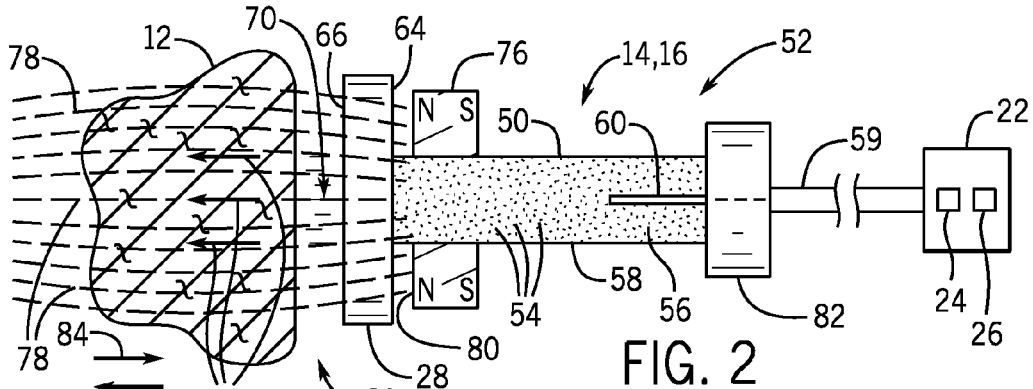
FIG. 2 is a cross-sectional side view of an embodiment of an electrode assembly of the system of FIG. 1.

FIG. 2 is a cross-sectional side view of an embodiment of the first electrode assembly 14 of FIG. 1. While the first electrode assembly 14 is illustrated, the second electrode assembly 16 may be similar to or mirror the first electrode assembly 14. The first electrode assembly 14 includes a hollow housing 50 made out of a dielectric material (e.g., polyoxymethylene, borosilicate glass, acrylic, polyamide, polytetrafluoroethylene (PTFE), acetal homopolymer, polyethylene (PE), polypropylene (PP), quartz, glass) that receives a fluid 52 (e.g., a multi-phase fluid). For example, the housing 50 may be a transparent or translucent dielectric housing 50 (e.g., a glass housing). In some embodiments, the fluid 52 may be a multi-phase fluid (e.g., solid/gas, solid/liquid, gas/liquid, solid/gas/liquid) that includes conductive material 54 (e.g., particles) in a conductive fluid 56 (e.g., gas and/or liquid) sealed in a cavity 58 within the housing 50. The conductive particles 54 may be a conductive non-ferromagnetic material (e.g., brass, copper, silver, aluminum, magnesium, platinum, carbon shavings, or dissolved salts) or a combination of non-ferromagnetic materials. In some embodiments, the conductive particles 54 may be randomly or uniformly shaped, and have shapes that are helical, spherical, rectangular, elongated, curved, wavy, etc. The fluid 56 may be a working gas mixture that includes noble gases (e.g., helium, neon, argon, krypton, xenon, radon) or a combination of a noble gas(s) with atmospheric gases (e.g., oxygen, nitrogen). In some embodiments, the fluid 56 may be a liquid (e.g., a saline solution).

In operation, the electrical signal from the controller 22 passes through a cable 59 (e.g., HV/RF feed cables) to a conductive non-ferromagnetic wire electrode 60 (e.g., tungsten) in the housing 50. In some embodiments, there may be more than one conductive non-ferromagnetic wire electrode 60 (e.g., 1, 2, 3, 4, 5, 6, 7, 8, 9, 10, or more). Embodiments with more than one conductive non-ferromagnetic wire electrode 60, may enable each electrode 60 to carry a different electrical signal (e.g., signals may differ in number of waves, frequency, amplitude) or the same electrical signal. As the electrical signal enters the housing 50, the fluid 52 conducts the electrical signal through the housing 50 to the dielectric barrier 28 where charge builds. In some embodiments, the dielectric barrier 28 may be integral to the housing 50 or may be a separately attached dielectric sheet or plate. Once a sufficient amount of charge builds on the first side 64 (e.g., proximal side) of the dielectric barrier 28, the multi-frequency harmonic-rich electrical signal crosses to the second side 66 (e.g., distal side) of the dielectric barrier 28 and across the air gap 30 forming cold plasma. As explained above, some embodiments may include a fluid 52 (e.g., a multi-phase fluid) with conductive material 54 (e.g., particles). It is believed that as the electrical signal enters the housing 50 the conductive particles 54 act as antennae that attenuate some frequencies as well as increase the capacitance (e.g., particles increase surface area available for storing charge), which may facilitate cold plasma formation.

As the multi-frequency, harmonic-rich electrical signal crosses the air gap 30, the gas molecules lose and gain electrons to form a multi-frequency, harmonic-rich plasma 70 between the dielectric barrier 28 and the biological tissue 12. To increase penetration of the energy 74, the first electrode assembly 14 may include a magnet 76 that forms a magnetic field 78 that guides and contains the cold plasma 70 and energy 74. For example, the magnet 76 may guide the cold plasma 70 and energy 74 along magnetic field lines and block or reduce movement of the cold plasma 70 and energy 74 outside of the magnetic field 78. In other words, the magnet 76 may focus the cold plasma 70 and energy 74, enabling the energy 74 and electrons in the cold plasma 70 to penetrate deeply into the target substrate 12 (e.g., biological tissue).

The magnet 76 may be a permanent magnet (e.g., neodymium magnets or magnets made out of a ferromagnetic metal) with a South pole oriented in axial direction 84 and a North pole oriented in axial direction 86 towards the dielectric barrier 28. In some embodiments, the magnet 76 may be an electromagnet coupled to the controller 22. The electromagnet 76 may include windings (e.g., 10, 50, 100, or more) that form the magnetic field 78. The polarity of the electromagnetic field may likewise be oriented with the North Pole facing in axial direction 86 and the South Pole facing axial direction 84. In operation, the controller 22 may increase or decrease the strength of the electromagnet 76 by increasing or decreasing the current flow through the electromagnet 76 (e.g., pulse). As illustrated, the magnet 76 may be next to dielectric barrier 28 or the magnet 76 may abut/contact the dielectric barrier 28. To block arcing, the dielectric barrier 28 may have an area that is 1, 5, 10, 15, 20, 25%, or greater than a side 80 of the magnet 76. Finally, the first electrode assembly 14 may include a mount 82 that couples to a fixture (e.g., a stand, an adjustable arm, etc.) that positions and orients the first electrode assembly with respect to the target substrate 12. In some embodiments, the mount 82 may couple directly to the housing 50 or may be integrally formed as part of the housing 50 (e.g., one-piece).

Figure 3:
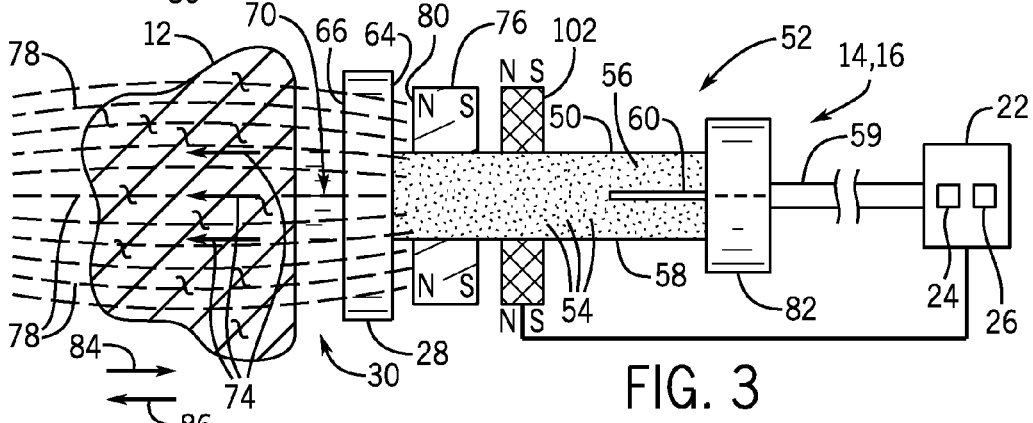
FIG. 3 is a cross-sectional side view of an embodiment of an electrode assembly the system of FIG. 1.

FIG. 3 is a cross-sectional side view of an embodiment of the first electrode assembly 14. The first electrode assembly in FIG. 3 operates like the first electrode assembly 14 in FIG. 2, and may also represent the second electrode assembly 16 of FIG. 1. The first electrode assembly 14 in FIG. 3 may include first and second magnets 76 and 102. As illustrated, the first magnet 76 may be a permanent magnet while the second magnet 102 is an electromagnet, or vice versa. However, in some embodiments, the first magnet 76 and the second magnet 102 may both be permanent magnets or electromagnets. The first magnet 76 may be made out of neodymium or another ferromagnetic material, while the second magnet 102 may include windings (e.g., 10, 50, 100, or more) that form a magnetic field as current flows through the wires. In some embodiments, the order of the first and second magnets 76, 102 may be reversed with the second electromagnet 102 placed next to the dielectric barrier 28, instead of the first permanent magnet 76. As illustrated, the first and second magnets 76 and 102 are positioned so that the South poles are oriented in axial direction 84 and the North poles are oriented in axial direction 86. Together the first and second magnets 76, 102 form a magnetic field 78 that guides and focuses the cold plasma 70 while enabling electrons in the cold plasma 70 and energy 74 to deeply penetrate the target substrate 12.

Figure 4:
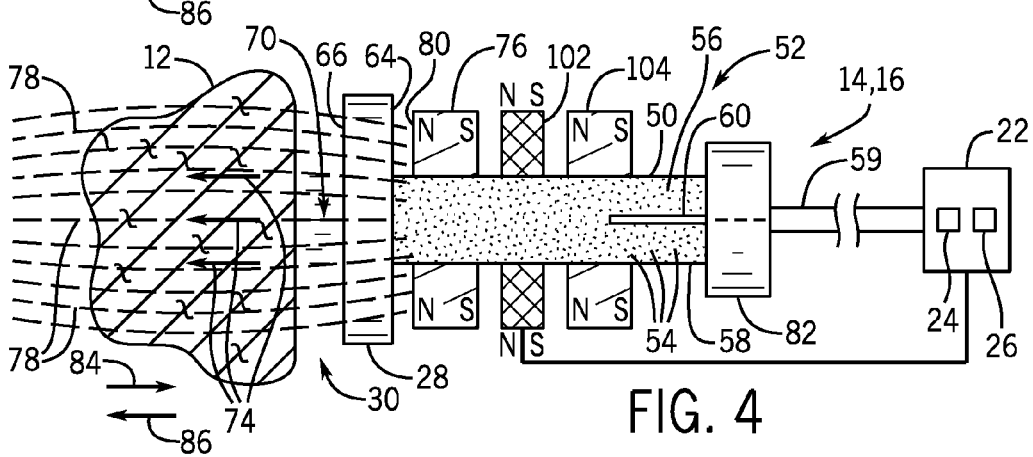
FIG. 4 is a cross-sectional side view of an embodiment of an electrode assembly the system of FIG. 1.

FIG. 4 is a cross-sectional side view of an embodiment of the first electrode assembly 14. The first electrode assembly 14 in FIG. 4 operates like the first electrode assembly 14 in FIGS. 2 and 3, and may also represent the second electrode assembly 16 of FIG. 1. The first electrode assembly 14 in FIG. 4 may include the first magnet 76, the second magnet 102, and a third magnet 104 to increase the strength of the magnetic field 78. As illustrated, the first magnet 76 may be a permanent magnet, the second magnet 102 may be an electromagnet, and the third magnet 104 may also be a permanent magnet. However, in some embodiments the first magnet 76, the second magnet 102, and the third magnet 104 may all be permanent magnets, electromagnets, or another combination thereof. As explained above, the first and third magnets 76, 120 may be formed out of neodymium or another ferromagnetic material, while the second magnet 102 may include windings (e.g., 10, 50, 100, or more) that form a magnetic field 78 as current flows through the wires.

In some embodiments, the order of the magnets 76, 102, and 104 may be reversed or have a different order. For example, the second magnet 102 may be placed nearer the dielectric barrier 28, with the first magnet 76 and the third magnet 104 placed behind the second magnet 102. The polarity of the first magnet 76, the second magnet 102, and the third magnet 104 are placed so that their South poles are oriented in axial direction 84 and the North poles are oriented in axial direction 86 towards the dielectric barrier 28. Together the first magnet 76, the second magnet 102, and the third magnet 104 form a magnetic field 78 that guides and focuses the cold plasma 70 and energy 74, enabling electrons in the cold plasma 70 and energy 74 to deeply penetrate the target substrate 12.

Figure 5:
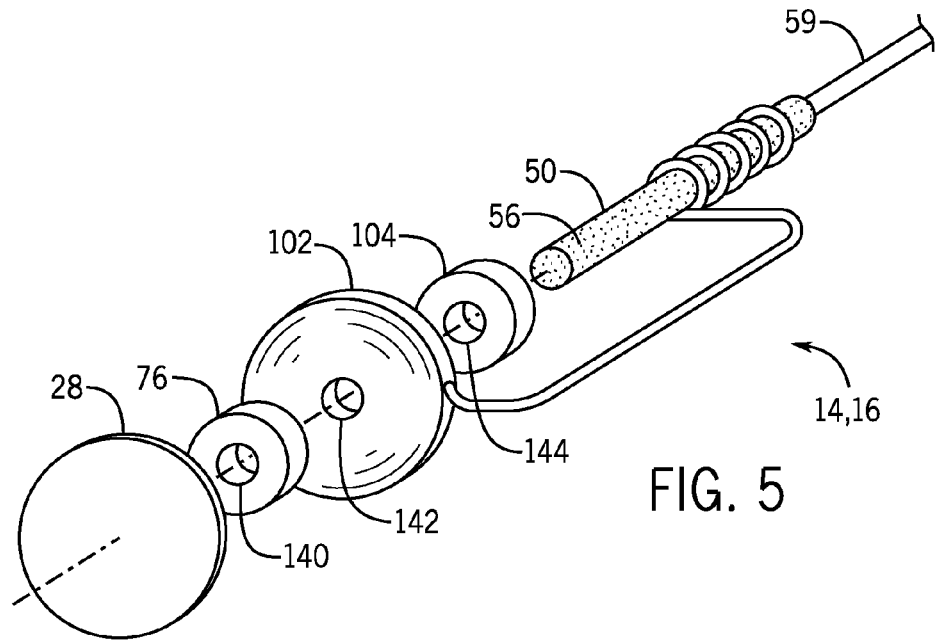
FIG. 5 is a perspective partial exploded view of an embodiment of an electrode assembly the system of FIG. 1.

FIG. 5 is a perspective partially exploded view of an embodiment of the first electrode assembly 14, and may also represent the second electrode assembly 16 of FIG. 1. As illustrated, the first magnet 76, the second magnet 102, and the third magnet 104 are cylindrical (e.g., disc-shaped magnets), and include respective first, second, and third apertures 140, 142, and 144. The apertures 140, 142, and 144 enable the magnets 76, 102, and 104 to circumferentially surround the housing 50 (e.g., cylindrical housing) and provide the magnetic field 78 that guides and contains the cold plasma 70 and energy 74. In some embodiments, the housing 50 may have a shape other than cylindrical (e.g., square, rectangular, oval, etc.). Likewise, the magnets 76, 102, and 104, though cylindrical in FIG. 5, may have other shapes (e.g., square, rectangular, oval, etc.). In some embodiments, the shape of the magnets 76, 102, and 104 may not correspond to the shape of the housing 50. For example, the first electrode assembly 76 may enable customization of the magnetic field 78 by including differently shaped magnets 76, 102, and 104 that then influence the shape of the cold plasma 70 as well as penetration of electrons in the cold plasma 70 and energy 74 into the target substrate 12.

Figure 6:
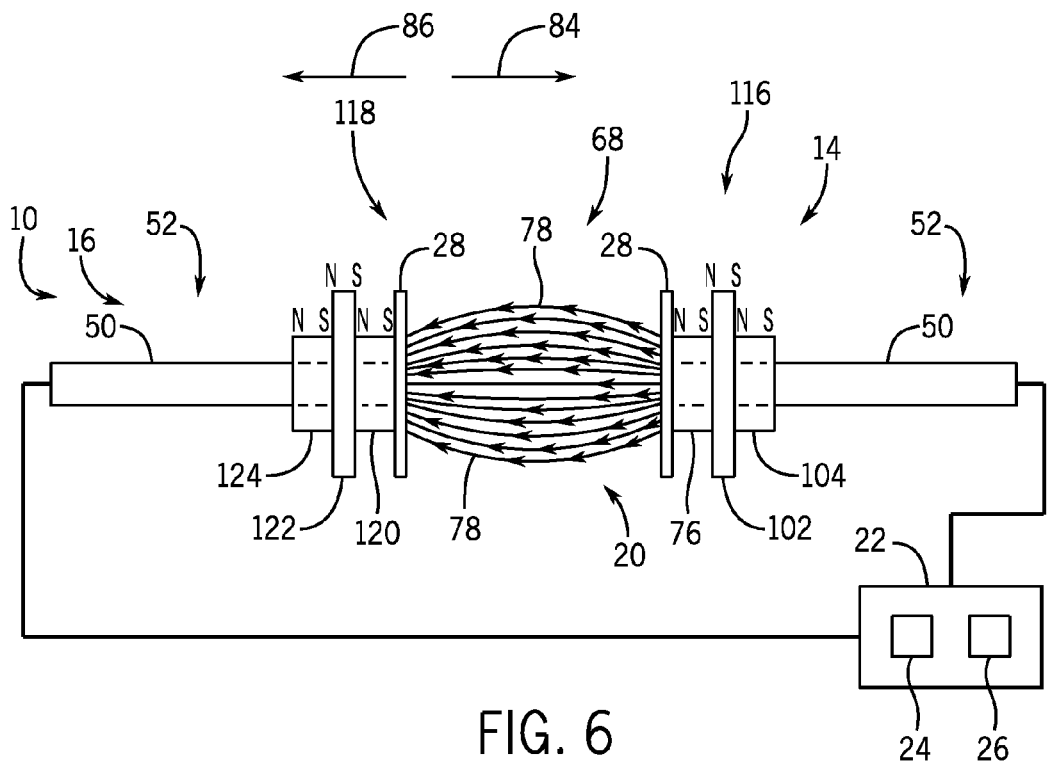
FIG. 6 is a side view of an embodiment of a first electrode assembly and a second electrode assembly the system of FIG. 1.

FIG. 6 is a side view of an embodiment of the first electrode assembly 14 and a second electrode assembly 16, as shown in FIG. 1. As explained above, the first electrode assembly 14 may be a powered electrode and the second electrode assembly 16 may be a ground electrode. In operation, the second electrode assembly 16 electrically attracts plasma and energy, formed by the first electrode assembly 14, enabling electrons in the plasma and RF energy to penetrate a target substrate 12 to significant depths (e.g., 1, 2, 3, 4, 5, 10, 20, 30, 40, or more centimeters) and/or in focal regions. As illustrated, the first electrode assembly 14 couples to a controller 22 that provides a multi-frequency, harmonic-rich electrical signal (e.g., a timed pulse electrical signal pulsed between 100-700 Hz with an output voltage between 1-100 KV peak-peak having multiple A/C waves at multiple frequencies, that overlap to produce 2-2,000,000 or more harmonic components between DC and 500 MHz). When the multi-frequency, harmonic-rich electrical signal enters the housing 50, the fluid 52 conducts the signal to the dielectric barrier 28. In some embodiments, the fluid 52 may be a multi-phase fluid that changes the electrical signal (e.g., attenuates some of the frequencies) with the conductive particles 54. The attraction of the electrical signal to ground enables the electrical signal to pass through the dielectric barrier 28 and into the air gap 30. As the multi-frequency, harmonic-rich electrical signal contacts gas molecules in the air gap 30, the electrical signal removes electrons from some of the gas molecules at low energy levels to form a low temperature plasma with positive ions, negative ions, and electrons. The electrons in the cold plasma and energy from the first electrode assembly 14 then pass through the air gap 30 and substrate 12 to the second electrode assembly 16.

As illustrated, the first electrode assembly 14 may include one or more magnets 116 and the second electrode assembly 16 may include one or more magnets 118. It is believed that the magnets 116 on the first electrode assembly 14 and the magnets 118 on the second electrode assembly 16 form a magnetic field 78 that contains and focuses the cold plasma and energy. In some embodiments, the first electrode assembly 14 includes a first permanent magnet 76, an electromagnet 102, and a second permanent magnet 104; and the second electrode assembly 16 similarly includes a first permanent magnet 120, an electromagnet 122, and a second permanent magnet 124. However, the first electrode assembly 14 and the second electrode assembly 16 may vary in the number of magnets (e.g., 1, 2, 3, 4, 5, or more), strength of the magnets (e.g., size, material type, or windings), shape of the magnets, order of the magnets, and type of magnets (e.g., electromagnetic vs. permanent magnets). As illustrated, the magnets 116 and 118 have a magnetic polarity with the North Pole oriented in axial direction 86 and the South Pole oriented in axial direction 84. When placed on opposite sides of target substrate 12 (e.g., biological tissue), the orientation of the magnets 116 and 118 attracts the first electrode assembly 14 to the second electrode assembly 16 to form a magnetic field 78 through the target substrate 12 that facilitates and guides energy transfer. In some embodiments, electromagnets 102 and 122 may be pulsed electromagnets that are synchronized by the controller 22 to provide coupled electromagnetic fields that energize at alternating times creating a push/pull effect through the target substrate 12. In some embodiments, electromagnets 102 and 122 may have opposing fields to limit and control depth of penetration in order to create a more shallow and limited treatment zone.

Figure 7:
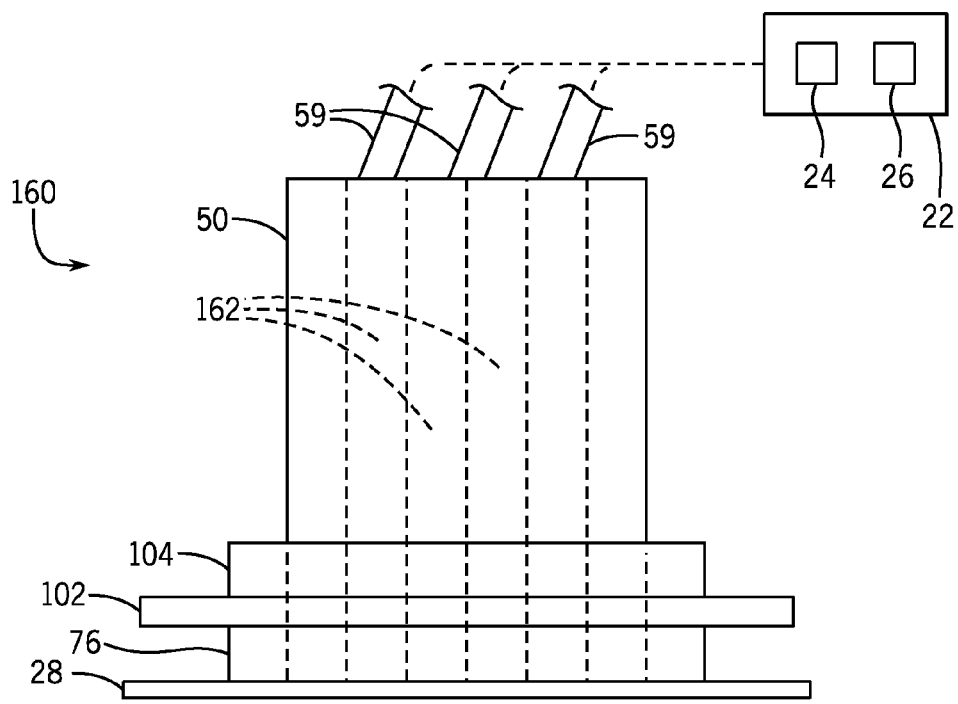
FIG. 7 is a side view of an embodiment of an electrode assembly the system of FIG. 1.

FIG. 7 is a side view of an electrode assembly 160. The electrode assembly 160 includes a dielectric barrier 28, a first permanent magnet 76, a second electromagnet 102, a third magnet 104, and a housing 50. Similar to the electrode assemblies 14, 16 discussed above, the electrode assembly 160 may vary in the number of magnets (e.g., 1, 2, 3, 4, 5, or more), strength of the magnets (e.g., size, material type, or windings), shape of the magnets, order of the magnets, and type of magnets (e.g., electromagnetic vs. permanent magnets). Moreover, the housing 50 may include multiple sub-housings 162 (e.g., 1, 2, 3, 4, 5, 6, 7, 8, 9, 10, or more) made out of a dielectric material (e.g., polyoxymethylene, borosilicate glass, acrylic, polyamide, polytetrafluoroethylene (PTFE), acetal homopolymer, polyethylene (PE), polypropylene (PP), quartz, glass). The multiple sub-housings 162 receive a fluid 52. The fluid 52 may be a single-phase conductive fluid or multi-phase fluid (e.g., solid/gas, solid/liquid, solid/liquid/gas) that includes conductive material 54 (e.g., particles) in a fluid 56 (e.g., gas and/or liquid) sealed in a cavity 58 within the housing 50. For example, the conductive particles 54 may be a conductive non-ferromagnetic material (e.g., brass, copper, silver, aluminum, magnesium, platinum, carbon shavings, or dissolved salts) or a combination of conductive materials. The fluid 56 may be a working gas mixture that includes noble gases (e.g., helium, neon, argon, krypton, xenon, radon) or a combination of a noble gas(s) with atmospheric gases (e.g., oxygen, nitrogen). In operation, the controller 22 transfers a multi-frequency, harmonic-rich electrical signal (e.g., a timed pulse electrical signal pulsed between 100-700 Hz with an output voltage between 1-100 KV peak-peak having multiple A/C waves at multiple frequencies, that overlap to produce 2-2,000,000 or more harmonic components between DC and 500 MHz) through the electrodes 60 into the fluid 52 in the sub-housings 162. In some embodiments, each sub-housing 162 may receive the same or a different electrical signal (e.g., the signal may differ in number of waves, power, amplitude, and frequencies). Moreover, each of the sub-housings 162 may be filled with a different fluid 52 (e.g., different conductive particles 54 and/or fluid 56). The differences in the fluids 52 and electrical signals may enable the electrode assembly 160 to vary the types of cold plasma for different applications and treatments or the amount of cold plasma created (e.g., activate one or more of the sub-housings 162, vary energy output, etc.). For example, each sub-housing 162 may be customized to a particular medical treatment type (e.g., deep tissue energy treatment, surface infection treatment, etc.) or customized to treat a specific part of the body (e.g., arm, leg, chest, head, neck, foot, hand, etc.) with a particular tissue composition.

Figure 8:
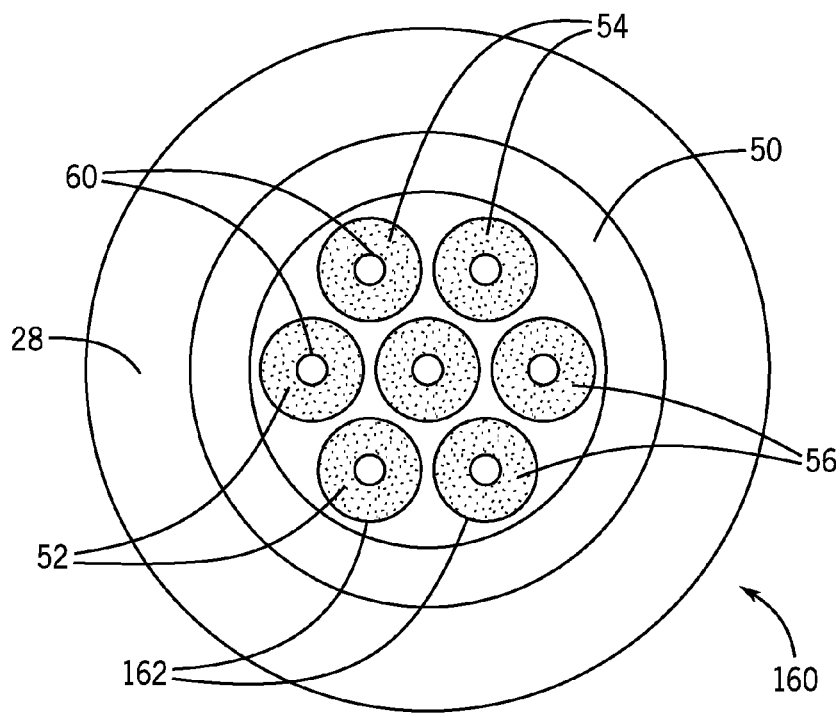
FIG. 8 is a front view of an embodiment of the electrode assembly in FIG. 8.

FIG. 8 is a front view of the electrode assembly 160 in FIG. 8. As illustrated, the electrode 160 includes multiple sub-housings 162 (e.g., six peripheral housings 162 around a central housing 162). The sub-housings 162 may include respective electrodes 60 and fluid 52. In some embodiments, the fluid 52 may vary between the sub-housings 162 (e.g., type of non-ferromagnetic material(s), liquid vs. gas, percentage of non-ferromagnetic material within the housing, etc.). Furthermore, the size of the sub-housings 162 may differ. For example, instead of equally sized sub-housings 162 some of the sub-housings 162 may be larger than others (e.g., a large center sub-housing 162 with smaller sub-housings 162 that circumferentially surround the center sub-housing 162). The differences in the sub-housings 162 may influence parameters of plasma and energy production for different kinds of treatments.

Figure 9:
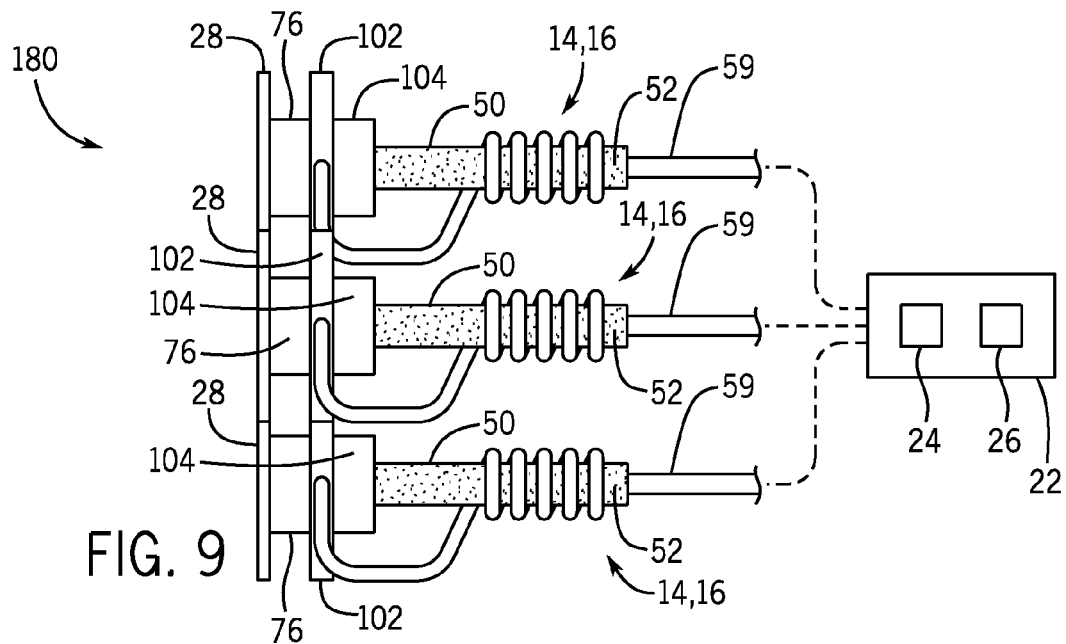
FIG. 9 is a side view of an embodiment of an electrode assembly of the system of FIG. 1.

FIG. 9 is a side view of an embodiment of an electrode assembly 180. The electrode assembly 180 may include multiple electrode assemblies 14 or 16 coupled together (e.g., 1, 2, 3, 4, 5, 6, 7, 8, 9, 10, or more). In other words, the electrode assembly 180 is scalable depending on the application (e.g., increased coverage area). For example, the electrode assembly 180 may include a single row or multiple rows of electrode assemblies 14, 16 that form a grid. In some embodiments, the electrode assembly 180 may include electrode assemblies 14, 16 that are angled with respect to each other enabling focused treatment on a particular point within a target substrate (e.g., concentrate multiple electrode assemblies 14, 16 on a specific location). As illustrated, the electrode assemblies 14 include a first permanent magnet 76, a first electromagnet 102, and a second permanent magnet 104. However in some embodiments, the electrode assemblies 14 may vary with respect to each other in the number of magnets (e.g., 1, 2, 3, 4, 5, or more), shape of the magnets, strength of the magnets (e.g., size, material type, or windings), order of the magnets, and type of magnets (e.g., electromagnetic vs. permanent magnets). The electrode assemblies 14 may also vary in the type of fluid 52 in the housing 50 (e.g., a single-phase conductive fluid, multi-phase fluid). The differences between the electrode assemblies 14 may enable a customized treatment with different types of cold plasma and energy covering different areas of a target substrate. Furthermore, one or more controllers 22 may control the electrode assemblies 14 by varying the multi-frequency, harmonic-rich electrical signal sent to the electrodes 60. For example, the controller 22 may turn on only some of the electrode assemblies 14 depending on the area of treatment and/or vary the electrical signal to change the energy and the cold plasma produced by the electrode assembly 180.

Figure 10:
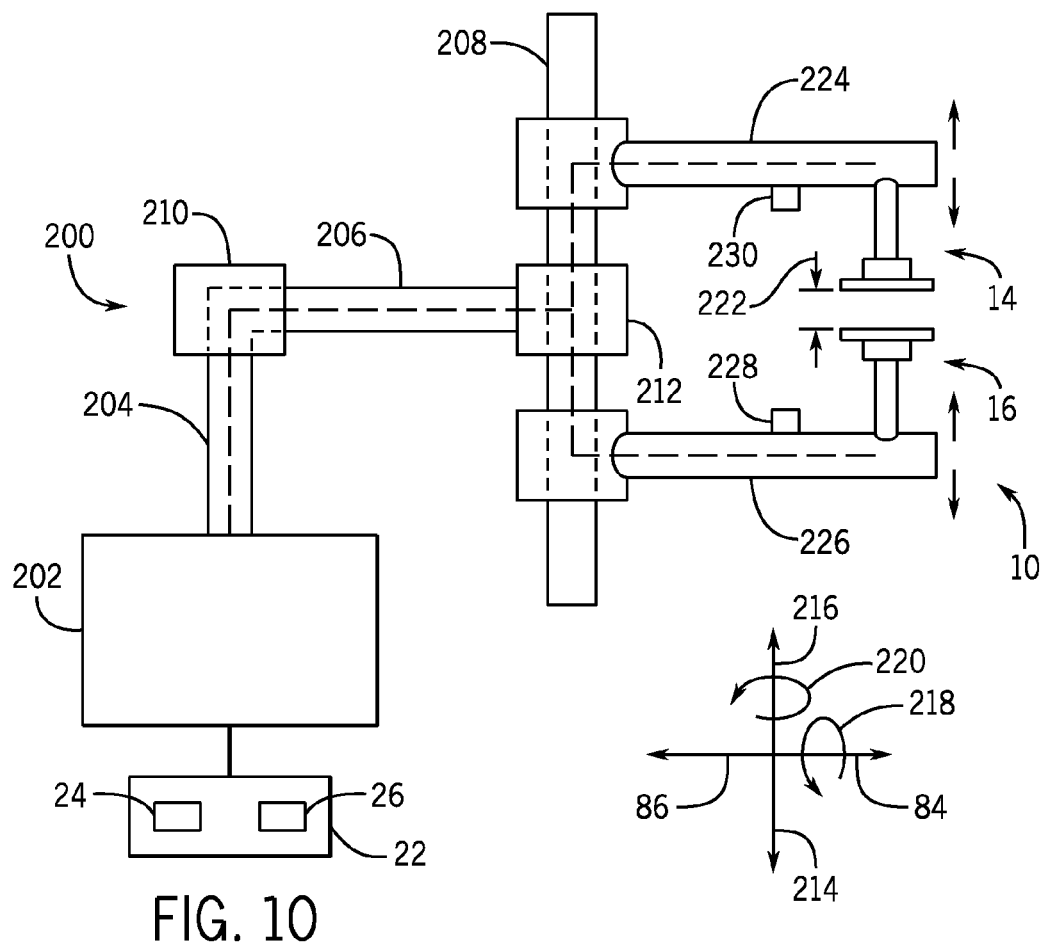
FIG. 10 is a side view of an embodiment of a fixture system capable of positioning a directional dielectric barrier discharge energy system.

FIG. 10 is a side view of an embodiment of a fixture system 200 capable of positioning the directional DBD energy system 10 manually and/or automatically with the controller 22. As illustrated, the system 200 includes a base 202 with multiple linkages 204, 206, and 208 that couple together with joints 210 and 212. The joints 210 and 212 enable linkages 204, 206, and 208 to move axially along directions 84, 86, 214, and 216 as well as rotate in directions 218 and 220. Furthermore, the fixture system 200 may include arms 224 and 226 that change the distance 222 between the first and second electrode assemblies 14, 16. As illustrated, the arms 224 and 226 are repositionable on the linkage 208 enabling the first and second electrode assemblies 14 and 16 to move closer together or farther apart along the linkage 208, depending on the thickness of the target substrate 12 (e.g., biological tissue). In operation, the controller 22 may control the overall positioning and distance between the electrode assemblies 14 and 16 with feedback from sensors 228 and 230, input from an operator, and/or feedback from an imaging system that detects a plasma treatment area (e.g., x-ray, CT scan, ultrasound). For example, the controller 22 may execute instructions that drive motors in the joints 210 and 212; and in the arms 224 and 226 that position and orient the electrode assemblies 14 and 16 about a target substrate. In some embodiments, the instructions may include a treatment protocol with treatment pattern instructions for moving the directional DBD energy system 10 during treatment (e.g., a treatment pattern that includes circular motion, figure-8 motion etc. about a target). The controller 22 may also execute treatment protocols that change the energy and cold plasma production by the directional DBD energy system 10 for different treatments (e.g., surface treatment, deep penetration treatment, etc.). In still other embodiments, the controller 22 may move the electrode assemblies 14 and 16 to different locations on a target while producing cold plasma, enabling the directional DBD energy system 10 to treat multiple locations on a patient or other substrate, in a single operation.

Figure 11:
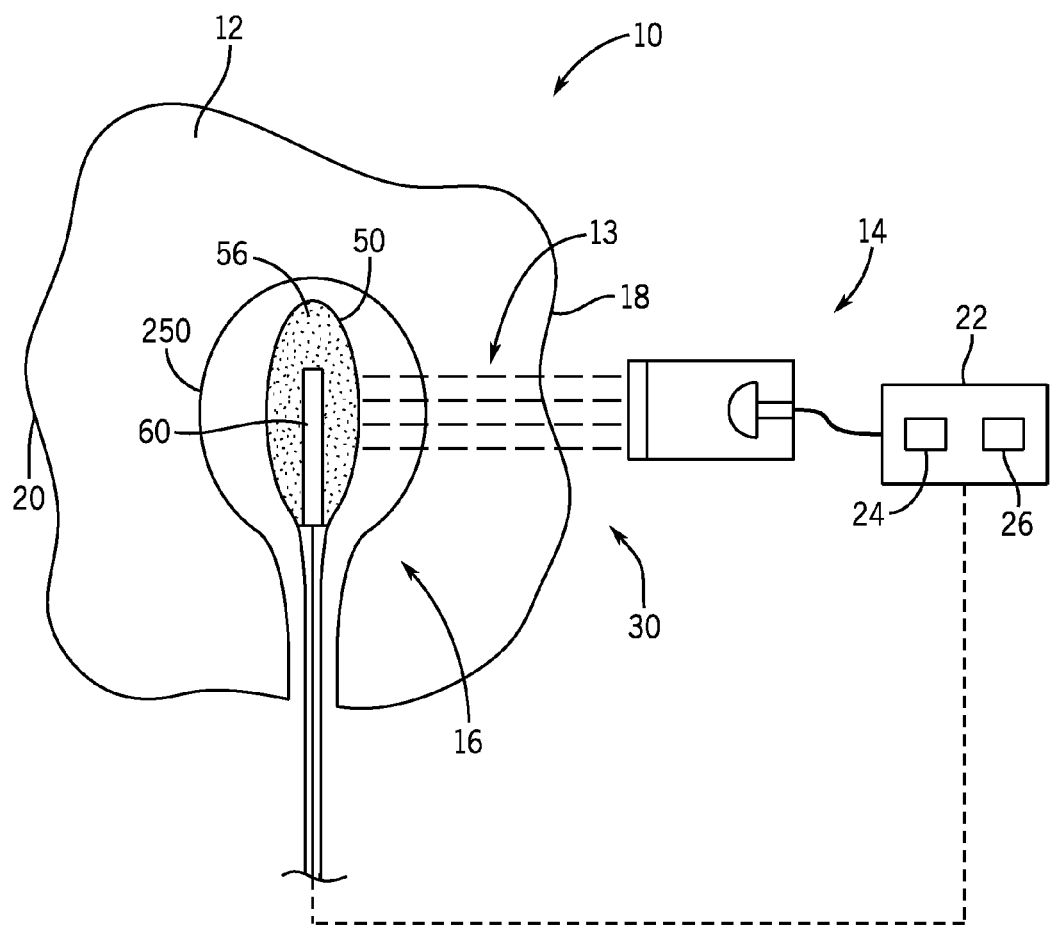
FIG. 11 is a cross-sectional side view of an embodiment of a directional dielectric barrier discharge energy system.

FIG. 11 is a cross-sectional side view of an embodiment of a directional dielectric barrier discharge (DBD) energy system 10. As explained above, the directional DBD energy system 10 may produce cold plasma and/or RF energy capable of penetrating deep into or through a target substrate 12 (e.g., osteological, connective, muscular, nervous, and epithelial tissues in humans and animals) to treat a plasma treatment area 13. The directional DBD energy system 10 may include a first electrode assembly 14 and a second electrode assembly 16. However, instead of positioning a first electrode assembly 14 on a first side 18 and the second electrode assembly 16 on a second side 18 of the target substrate 12, one of the electrode assemblies 14, 16 may be placed within a cavity 250 (e.g., body cavity, surgical openings, wound openings). In another embodiment, the first or second electrode assemblies 14, 16 may be placed within a lumen, which is then inserted into the target substrate 12 (e.g., through veins, etc.). As illustrated, the second electrode assembly 16 may rest within a cavity 250, and may be a grounded or powered electrode assembly. For example, in one embodiment, the second electrode assembly 16 is a grounded electrode assembly that attracts plasma and energy from the first electrode assembly 14. In another embodiment, the second electrode assembly 16 may be a powered electrode assembly that receives an electrical signal from the controller 22.

In operation, the controller 22 produces an electrical signal that enables the first electrode assembly 14 to produce cold plasma and energy. Specifically, the controller 22 uses the processor 24 to execute instructions stored in the memory 26 to produce and control the electrical signal (e.g., change power, amplitude, frequency/frequencies, pulse timing, etc.). The first electrode assembly 14 receives the electrical signal enabling the first electrode assembly 14 to generate cold plasma in the air gap 30. As the first electrode assembly 14 produces cold plasma and energy, the second electrode assembly 16 (e.g., ground) attracts and focuses the energy and cold plasma toward the plasma treatment region 13 on the target substrate 12. In other words, the second electrode assembly 16 may assist in guiding and or drawing electrons in the plasma stream and energy from the first electrode assembly 14 through the target substrate 12. For example, the second electrode assembly 16 may enable energy and electron penetration through 1, 2, 3, 4, 5, 10, 20, 30, 40, or more centimeters of biological tissue.

As illustrated, the second electrode assembly 16 may include a non-ferromagnetic wire electrode 60 within a housing 50 (e.g., a transparent or translucent dielectric). In some embodiments, the housing 50 may include the fluid 56. The fluid 56 may be a working gas mixture that includes noble gases (e.g., helium, neon, argon, krypton, xenon, radon) or a combination of noble gas(s) with atmospheric gases (e.g., oxygen, nitrogen, a saline solution, urine, or other biological fluid). By including fluid 56 within the housing 50, the second electrode assembly 16 may facilitate plasma formation within the cavity 250. For example, energy from the first electrode assembly 14 may enable charge to build on the housing 50 (e.g., dielectric barrier). Once a sufficient amount of charge builds on the housing 50, the charge may cross through the dielectric and the fluid 56 to the ferromagnetic wire electrode 60. As the charge passes through the fluid 56, the charge converts the fluid 56 into cold plasma within the housing 50. The cold plasma within the housing 50 may then produce energy for treatment around the cavity 250 while producing ultraviolet light that can kill bacteria and viruses within the target substrate 12.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A system comprising:
a directional dielectric barrier discharge (DBD) energy system, comprising:
  a first electrode assembly configured to generate energy, comprising:
    a first housing having a first fluid disposed in a first chamber;
    a first magnet, wherein the first magnet is configured to help guide or contain the energy generated by the first electrode assembly; and
    a first dielectric barrier.

2. The system of claim 1, wherein the directional DBD energy system is configured to generate a cold plasma.

3. The system of claim 2, wherein the first magnet comprises a permanent magnet and is configured to help guide or contain the cold plasma.

4. The system of claim 2, comprising a second magnet configured to help guide or contain the cold plasma and energy, wherein the second magnet comprises an electromagnet with windings in a first direction.

5. The system of claim 4, comprising a third magnet configured to guide the cold plasma and energy, wherein the third magnet comprises a permanent magnet.

6. The system of claim 5, wherein the first dielectric barrier couples to the first magnet, the first magnet couples to the second magnet, and the second magnet couples to the third magnet.

7. The system of claim 1, comprising a first conductive material in the conductive fluid.

8. The system of claim 1, wherein the first conductive material comprises non-ferromagnetic particles.

9. The system of claim 1, wherein the directional DBD energy system comprises a second electrode assembly, comprising:
 a second housing having a second fluid;
 a conductive line coupled to the second housing or ground;
 a fourth magnet coupled to the second housing, wherein the fourth magnet is configured to help guide or contain a cold plasma and the energy; and
 a second dielectric barrier,
 wherein the first electrode assembly is configured to be positioned on a first side of a substrate and the second electrode assembly is configured to be positioned axially opposite the first electrode assembly on a second side of the substrate.

10. The system of claim 9, wherein a polarity of the fourth magnet is oriented in the same direction as the first magnet, and wherein the first magnet and the fourth magnet are configured to help guide and contain the cold plasma.

11. The system of claim 9, wherein the second electrode assembly comprises a fifth and sixth magnet configured to help guide and contain the cold plasma.

12. A system comprising:
 a directional dielectric barrier discharge (DBD) energy system configured to generate energy, comprising:
 a first electrode assembly configured to be positioned on a first side of a substrate; and
 a second electrode assembly, wherein the second electrode is configured to be positioned on a second side of a substrate.

13. The system of claim 12, wherein directional DBD energy system is configured to generate a cold plasma, and wherein the first electrode assembly comprises a first magnet configured to help guide and contain the cold plasma and the energy.

14. The system of claim 13, wherein the second electrode assembly comprises a second magnet configured to help guide and contain the cold plasma and the energy.

15. The system of claim 12, comprising a controller configured to control the first electrode assembly, the second electrode assembly, or both to generate the cold plasma to treat the substrate with a plasma treatment protocol.

16. The system of claim 15, comprising a fixture configured to maintain the first electrode assembly and the second electrode assembly in a co-axial relationship during operation.

17. A system comprising:
 a directional dielectric barrier discharge (DBD) energy system configured to generate energy, comprising:
 a first electrode assembly comprising:
 a first housing having a first fluid in a first chamber; and
 a second housing having a second fluid in a second chamber.

18. The system of claim 17, comprising a second electrode assembly comprising a third housing having a third fluid disposed in a third chamber and a fourth housing having a fourth fluid disposed in a fourth chamber, wherein the first and second electrode assemblies are spaced apart from one another about a treatment area.

19. The system of claim 17, wherein the directional DBD energy system is configured to generate a cold plasma, and wherein a first magnet surrounds the first housing and a second magnet surrounds the second housing, and wherein the first magnet and the second magnet are configured to help guide and contain the cold plasma and energy.

20. The system of claim 17, wherein the first or second housing is configured to be placed within a target cavity.

* * * * *